United States Patent
Alheidt

(10) Patent No.: US 8,574,202 B2
(45) Date of Patent: Nov. 5, 2013

(54) POSITIVE DISPLACEMENT FLUSH SYRINGE

(75) Inventor: Thomas Adam Alheidt, Lake Stockholm, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 841 days.

(21) Appl. No.: 12/166,632

(22) Filed: Jul. 2, 2008

(65) Prior Publication Data

US 2008/0262439 A1    Oct. 23, 2008

Related U.S. Application Data

(63) Continuation of application No. 10/754,870, filed on Jan. 9, 2004, now abandoned.

(51) Int. Cl.
*A61M 5/315* (2006.01)

(52) U.S. Cl.
USPC .......................................... 604/229; 604/210

(58) Field of Classification Search
USPC .................... 604/181, 187, 228, 229, 210
See application file for complete search history.

(56) References Cited

U.S. PATENT DOCUMENTS

| | | | |
|---|---|---|---|
| 3,303,846 A | 2/1967 | Ogle | |
| 3,331,538 A | 7/1967 | Higgins | |
| 3,618,603 A | 11/1971 | Levenson | |
| 4,064,879 A | 12/1977 | Leibinsohn | |
| 4,664,128 A | 5/1987 | Lee | |
| 4,781,684 A | 11/1988 | Trenner | |
| 4,950,240 A | 8/1990 | Greenwood et al. | |
| 5,006,114 A | 4/1991 | Rogers et al. | |
| 5,106,372 A | 4/1992 | Ranford | |
| 5,147,333 A | 9/1992 | Raines | |
| 5,215,536 A | 6/1993 | Lampropoulos et al. | |
| 5,259,840 A | 11/1993 | Boris | |
| 5,370,620 A | 12/1994 | Shonfeld | |
| 5,509,433 A | 4/1996 | Paradis | |
| 5,795,337 A * | 8/1998 | Grimard | 604/222 |
| 5,807,374 A | 9/1998 | Caizza et al. | |
| 5,820,601 A | 10/1998 | Mayer | |
| 5,899,881 A | 5/1999 | Grimard et al. | |
| 5,902,271 A | 5/1999 | Jentzen | |
| 6,053,894 A | 4/2000 | Shadd | |

(Continued)

FOREIGN PATENT DOCUMENTS

WO    WO 01/97885    * 12/2001

OTHER PUBLICATIONS

"International Search Report" from International Appln PCT/US04/043203, 3 pgs.

(Continued)

*Primary Examiner* — Kevin C Sirmons
*Assistant Examiner* — Deanna K Hall
(74) *Attorney, Agent, or Firm* — Servilla Whitney LLC

(57) ABSTRACT

A positive displacement flush syringe includes a barrel having a chamber for retaining fluid and an elongate tip extending distally therefrom having a passageway therethrough in fluid communication with the chamber. A plunger having a stopper which is slidably positioned in said chamber for driving fluid out of the chamber by movement of the stopper relative to the barrel is provided. Further, structure is provided to move fluid distally in the passageway after fluid has been delivered from the chamber and the stopper is in contact with the distal wall of the chamber.

20 Claims, 13 Drawing Sheets

(56) References Cited

U.S. PATENT DOCUMENTS

| | | |
|---|---|---|
| 6,117,142 A | 9/2000 | Goodson et al. |
| 6,171,287 B1 | 1/2001 | Lynn et al. |
| 6,179,812 B1 | 1/2001 | Botich et al. |
| 6,206,861 B1 | 3/2001 | Mayer |
| 6,361,524 B1 | 3/2002 | Odell et al. |
| 6,361,528 B1 | 3/2002 | Wilson et al. |
| 2002/0107485 A1* | 8/2002 | Odell et al. ............ 604/187 |
| 2004/0010235 A1 | 1/2004 | Weilbacher et al. |
| 2004/0127859 A1 | 7/2004 | Ward |

OTHER PUBLICATIONS

"Written Opinion" from International Appln PCT/US04/043203, 6 pgs.

* cited by examiner

POSITIVE DISPLACEMENT FLUSH SYRINGE

CROSS-REFERENCE TO RELATED APPLICATIONS

This patent application is a continuation of and claims priority under 35 U.S.C. § 120 to, U.S. patent application Ser. No. 10/754,870 filed Jan. 9, 2004, the entire content of each being incorporated herein by reference.

BACKGROUND OF THE INVENTION

The present invention relates to syringe assemblies and particularly to syringe assemblies for use in flush procedures, for vascular access devices (VAD's). VAD's are commonly used therapeutic devices. There are two general classifications of VAD's, peripheral catheters and central venous catheters. If not properly maintained, VAD's can become occluded. To ensure VAD's are used properly and do not become occluded, standards of practice have been developed. These standards include a cleaning procedure, which is commonly referred to as a flush procedure or flushing a catheter.

VAD standards of practice usually recommend flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections. Flush procedures require different types and amounts of flush solutions. The most commonly used flush solutions are saline and or heparin lock solution. The type of flush solution and amount vary depending on the specific type of catheter. Flush solution volumes between 5 and 10 ml are most common but can range from 1 to 20 ml. Flush procedures also require that care be taken to prevent blood reflux into the catheter. Reflux in I.V. therapy is the term commonly used to describe the fluid that is drawn back into the catheter after a flush procedure. The concern is that the reflux fluid contains blood or solution that could cause the catheter to occlude. To ensure that reflux does not occur, flush procedures suggest two techniques: 1) at the end of the flush solution delivery, the user maintains pressure on the syringe plunger while clamping the I.V. line; or 2) while delivering the last 0.5 ml of flush solution disconnect the syringe from the I.V.port or clamp the I.V. line. Either technique maintains positive pressure on the fluid in the VAD to prevent reflux of fluid and blood.

For flush procedures, the I.V. line refers to the system containing a VAD, tubing set with clamp and may terminate with a port or valve. The most common types of I.V. ports are covered by pierceable septums or pre-slit septums and are known in the art and sometimes referred to as "PRN" from the Latin pro re nata meaning "as the need arises". The septum is preferably made of rubber or another elastomeric material, which permits insertion of a sharp needle cannula in order to infuse fluids or to withdraw fluids from the catheter. Upon withdrawal of the needle cannula the septum seals itself. Ports having pre-slit septums are used with blunt cannula or the frustoconically shaped tip of a syringe barrel. The syringe tip or the blunt cannula (which is usually attached to a syringe) is gently pushed through the pre-slit septum to establish fluid communication.

I.V. valves, another type of terminal I.V. access device that does not require a needle having a sharp tip, are activated by the frustoconically shaped tip of a syringe barrel to allow fluid communication between the interior of the syringe and the catheter. These valves may contain structure for delivering fluid from a storage compartment in the valve to the catheter, and are referred to in the art as positive displacement valves. Such a valve is taught in U.S. Pat. No. 6,206,861B1. Positive displacement valves were developed to overcome the reflux caused by the disconnection of a syringe tip or cannula from a port or valve. Unfortunately, the positive displacement valves were not designed to compensate for the worst-case syringe stopper induced reflux. When using a traditional syringe assembly containing an elastomeric stopper, the stopper is often compressed when it contacts the distal end of the syringe barrel at the completion of the flush procedure. If the user releases the pressure on the plunger after the flush solutions is delivered, the compressed stopper may expand back to its normal size drawing fluid back into the catheter. This fluid is referred to as syringe stopper induced reflux. Traditional syringe assemblies were designed to accurately deliver medications. Traditional syringe assemblies supplied by various suppliers may appear similar but can vary significantly in terms of performance especially stopper induced reflux. Because the catheter is inserted into the patient the users cannot see the reflux when it occurs and therefore cannot take corrective actions to address a potential problem.

Disconnection induced reflux and syringe stopper induced reflux would not be an issue if all users practice the positive pressure flushing techniques described hereinabove every time they flushed a VAD. However, user experience, environmental circumstance and patient condition vary significantly within the hospital setting and even more when one considers other areas that flush procedures are performed such as clinics and home care. As a result, VAD's are frequently occluded resulting in the need for additional professional time, declotting drugs, removal of catheters and new procedures to place new catheters. All of these interventions come at a cost to the healthcare system and its patients. It is desirable to have syringe assemblies that are designed for flush procedures to enhance best clinical practice. Specifically, syringe assemblies that are configured to automatically minimize or eliminate reflux without depending entirely on user technique. Further, the prior art focuses on syringe assemblies designed to deliver medications and not syringe assemblies that automatically provide additional small amount of flush solution in the I.V. line at the completion of the flush procedure.

Therefore there is a need for a simple, straight forward, automatic, easy-to-manufacture syringe assembly which helps reduce or eliminate reflux of blood into the catheter during and after the flush procedure has occurred even if flush procedures are not precisely followed. For example, prematurely releasing the compressive force on the plunger and/or removing the syringe from the I.V. line before it is clamped, may cause reflux of blood into the catheter, thus increasing the chance of VAD occlusion.

SUMMARY OF THE INVENTION

The present invention is directed to a syringe assembly for use in flush applications. The syringe assembly has structure to provide an additional positive displacement of flush solution after the flush solution has been substantially delivered from the cavity in the syringe barrel through the application of an additional distally-directed force to the plunger.

An I.V. flush syringe assembly comprises a barrel including a cylindrical side wall having an inside surface defining a chamber for retaining fluid, an open proximal end, and a distal end including a distal wall with an elongate tip extending distally therefrom having a passageway therethrough in fluid communication with the chamber. A plunger including an elongate body portion having a proximal end, a distal end, and a resilient stopper is slidably positioned in fluid-tight engagement with the inside surface of the barrel for drawing fluid into and driving fluid out of the chamber by movement of the stopper relative to the barrel. The elongate body portion extends outwardly from the open proximal end of the barrel. The barrel includes structure for moving fluid distally in the passageway after fluid has been delivered from the chamber and the stopper is in contact with the distal wall.

Structure for positively displacing additional fluid after the stopper has contacted the distal wall of the barrel comprises the stopper including a distal end having a distal surface and a proximal end having a cavity therein defining an inside surface. The distal end of the plunger is connected to the stopper by a complementary detent structure defining a first detent position and a second detent position. The detent structure is configured so that an additional distally-directed force applied to the plunger after fluid has been delivered from the chamber causes the plunger to move distally with respect to the stopper from the first detent position to the second detent position so that a distal tip on the distal end of the plunger contacts the inside surface of the stopper forcing part of the distal end of the stopper toward and preferably into the passageway to move fluid distally in the passageway.

The stopper may include a conically-shaped distal surface and a complementary conically-shaped inside surface of the barrel distal wall wherein the total included angle of the inside surface of the barrel at the distal wall is preferably greater than the total included angle of the stopper distal surface.

The stopper may include a distally-directed projection on the distal end of the stopper shaped to fit in the passageway when the plunger and the stopper are engaged in the second detent position.

The inside surface of the stopper may include a proximally-directed protuberance configured to contact the distal tip of the plunger when the plunger and the stopper are engaged in the second detent position.

The syringe assembly may be configured so that the inside surface of the stopper includes a first discontinuity, and a second discontinuity located distally from the first discontinuity. The distal end of the plunger includes a discontinuity positioned so that when the stopper and the plunger are in the first detent position the plunger discontinuity engages the first discontinuity in the stopper, and when the stopper and the plunger are in the second detent position, the plunger discontinuity engages the second discontinuity in the stopper. The discontinuity on the plunger may be a raised projection and the raised projection may be shaped like an annular ring or flange. The first discontinuity in the stopper may be a recess for containing the discontinuity on the plunger such as an annular recess. The first discontinuity may also be an inwardly directed projection and the plunger discontinuity a recess for accepting the projection.

The syringe assembly may also include flush solution in the chamber and a tip cap releasably connected to the tip of the syringe barrel for sealing the passageway. The flush solution may be selected from the group consisting of saline flush solution and heparin lock solution.

The syringe assembly may further include a needle assembly including a cannula having a proximal end, a distal end, and a lumen therethrough. A hub having an open proximal end containing a cavity and a distal end attached to the proximal end of the cannula so that the lumen is in fluid communication with the cavity of the hub. The needle assembly is removably attached to the tip of the barrel through engagement of the tip to the cavity of the hub so that the lumen is in fluid communication with the chamber of the barrel.

The stopper may be made of material selected from the list consisting of thermoplastic elastomers, natural rubber, synthetic rubber, thermoplastic materials and combinations thereof.

The syringe assembly may further include a spring between the distal tip of the plunger and the distal end of the plunger. The spring is configured to compress when the plunger moves to the second detent position with respect to the stopper.

The syringe assembly may also include the barrel and plunger having complementary detent structures defining a primary detent position and a secondary detent position to hold the position of the plunger relative to the barrel. The primary detent position being positioned to engage when fluid has been delivered from the chamber and the stopper is in contact with the distal wall. The secondary detent position is configured to engage upon application of an additional distally directed force to the plunger after the stopper has made contact with the distal wall. The complementary detent structure between the barrel and the plunger can include the barrel having a first discontinuity and a second discontinuity located distally from the first discontinuity, and a proximal end of the plunger including a discontinuity positioned so that when the plunger and the barrel are in the primary detent position the plunger discontinuity engages the first barrel discontinuity and when the plunger and the barrel are in the secondary detent position the proximal plunger discontinuity engages the secondary barrel discontinuity.

DETAILED DESCRIPTION

Figure 1:
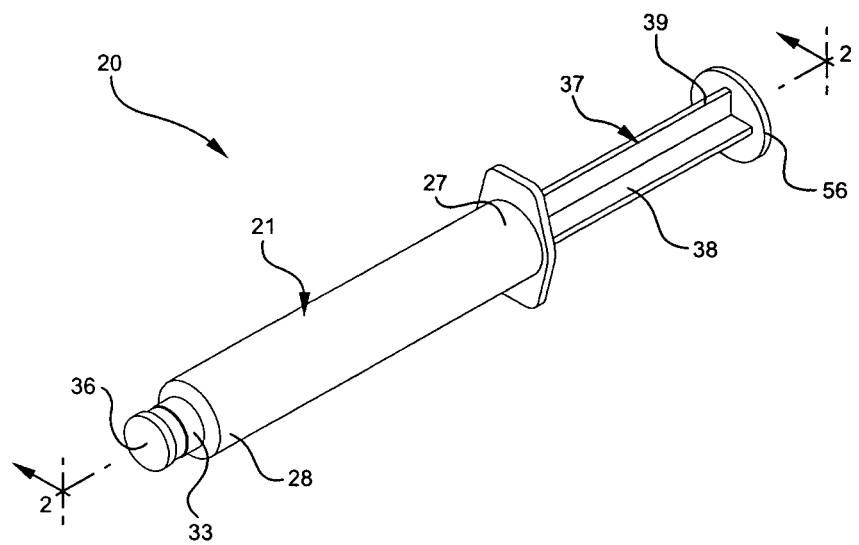
FIG. 1 is a perspective view of a syringe assembly of the present invention.
Figure 2:
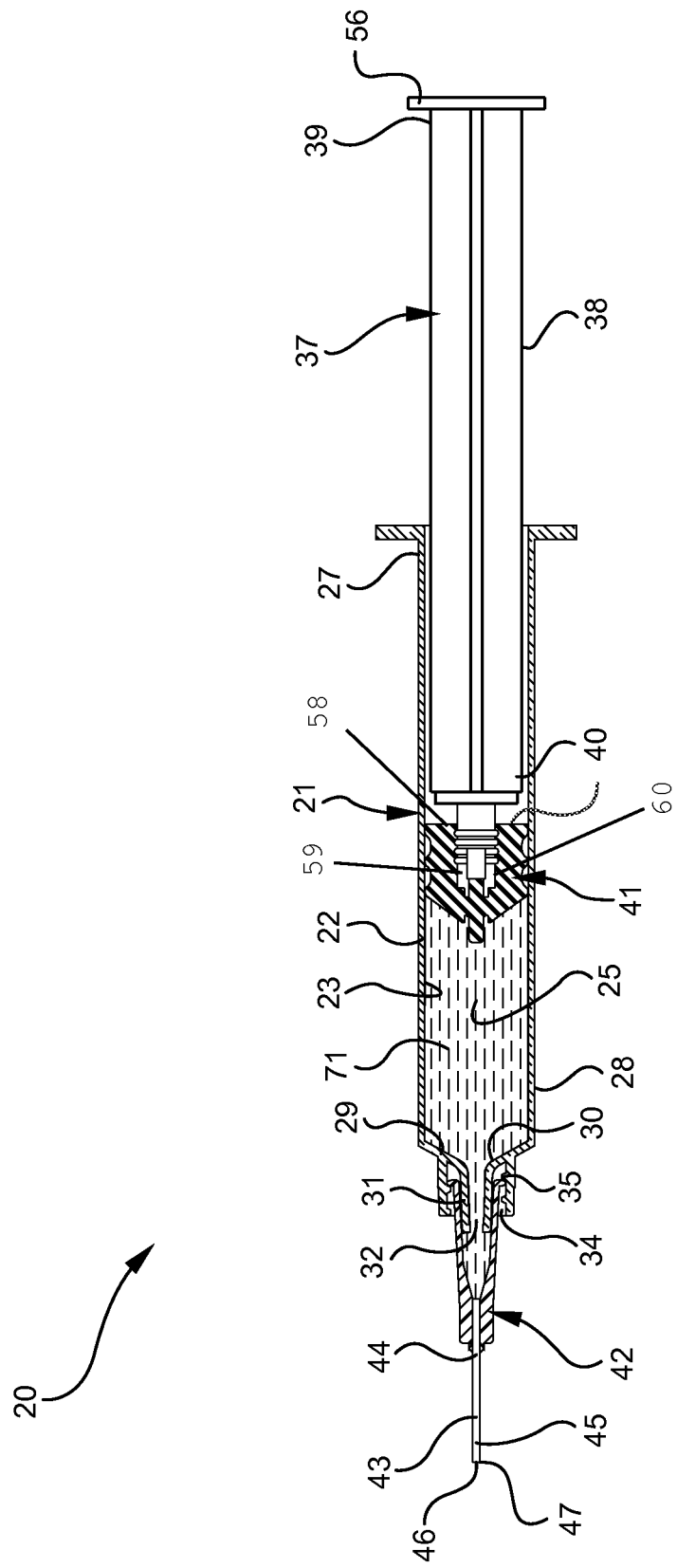
FIG. 2 is a partially cross-sectioned side elevational view of the syringe assembly of FIG. 1 with a needle assembly attached.
Figure 3:
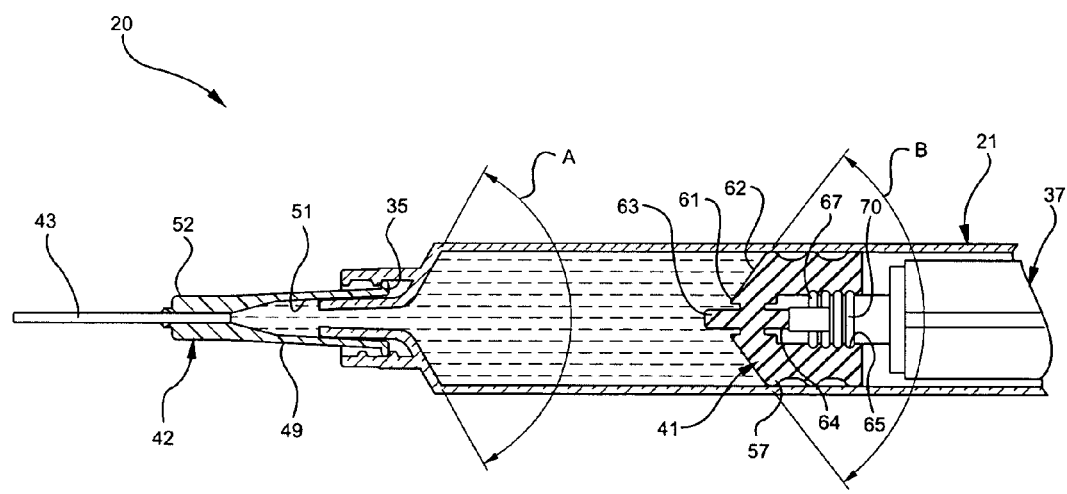
FIG. 3 is an enlarged partial cross-sectional side elevation view of the distal end of the syringe assembly of FIG. 2.

Referring to FIGS. 1-7, a syringe assembly 20 according to the present invention generally comprises a barrel 21, including a cylindrical side wall 22 having an inside surface 23 defining a chamber 25 for retaining fluid. The barrel further includes an open proximal end 27 and a distal end 28 having a distal wall 29 with an elongate tip 31 extending distally therefrom and having a passageway 32 therethrough in fluid communication with the chamber. The inside surface of the barrel at the distal wall, indicated as 30, is preferably conically shaped. The distal end of the barrel preferably, but not necessarily, includes a locking luer type collar 33 concentrically surrounding tip 31. The collar includes an inside surface 34 having at least one thread 35 thereon.

A cannula 43 includes a proximal end 44, a distal end 45 and a lumen 46 therethrough. The distal end of the cannula may include a sharp tip or a blunt tip 47 as shown. The cannula may be connected directly to the tip of the syringe barrel to establish fluid communication between the lumen and the chamber. Also, the cannula may be part of a needle assembly 42 including a hub 49 having an open proximal end 50 containing a cavity 51 and a distal end 52 attached to the proximal end of the cannula so that lumen of the cannula is in fluid communication with the cavity. The cavity of the hub can be removably frictionally engaged to the tip of the barrel.

Figure 4:
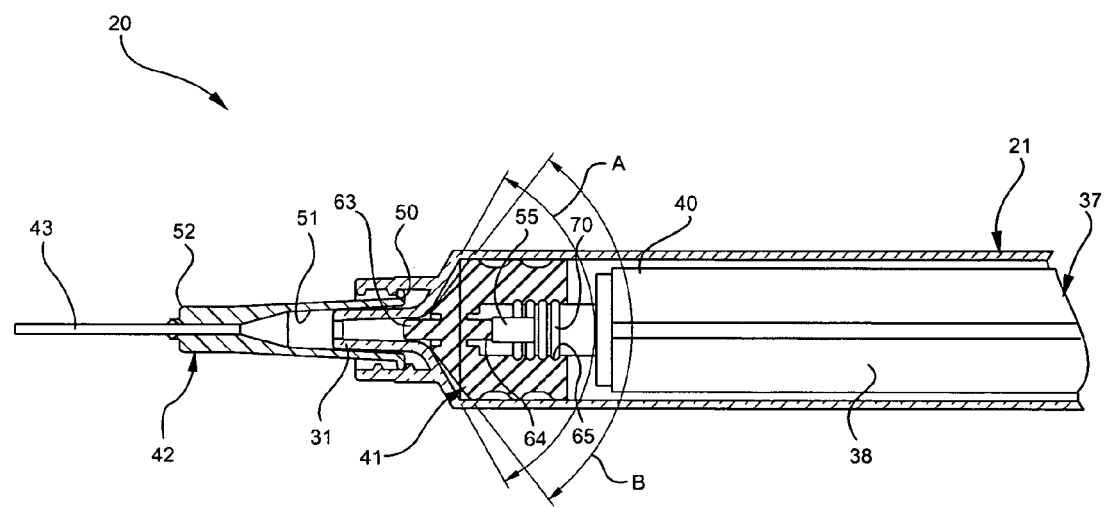
FIG. 4 is an enlarged partial cross-sectional side elevational view of the distal end of the syringe assembly shown at the completion of flush solution delivery.

A plunger 37 includes an elongate body portion 38, a proximal end 39 and a distal end 40. A stopper 41 is disposed on the distal end of the plunger rod through a structure that will be described in more detail hereinafter. Stopper 41 includes at least one rib and preferably a plurality of ribs 57 on its outside diameter. The stopper is slidably positioned in fluid-tight engagement with the inside surface of the barrel for drawing fluid into and driving fluid out of the chamber by movement of the stopper relative to the barrel. Elongate body portion of the plunger extends outwardly from the open proximal end of the barrel. Stopper 41 includes a proximal end 58 having a cavity 59 therein defining an inside surface 60. The stopper further includes a distal end 61 having a conically shaped distal surface 62 thereon. Conically-shaped distal surface 62 has a total included angle B as illustrated in FIG. 4. As will be explained in more detail hereinafter, total included angle A of the inside surface of the barrel at the distal wall is preferably greater than the total included angle B of the conically-shaped distal surface of the stopper in this embodiment.

The syringe assembly includes structure for moving fluid distally in passageway 31 after fluid has been delivered from chamber 25 and the distal surface of the stopper is in contact with the distal wall of the barrel.

The structure for moving fluid distally in the passageway after fluid has been delivered from the chamber includes the stopper being connected to the plunger by a complementary detent structure defining a first detent position and a second detent position. The detent structure is configured so that a distally directed force F applied to the plunger after fluid has been delivered from the chamber causes the plunger to move distally with respect to the stopper from the first detent position to the second detent position so that a distal tip 55 on the distal end of the plunger contacts inside surface 60 of the stopper forcing part of the distal end of the stopper into passageway 32 to move fluid distally in the passageway.

Figure 5:
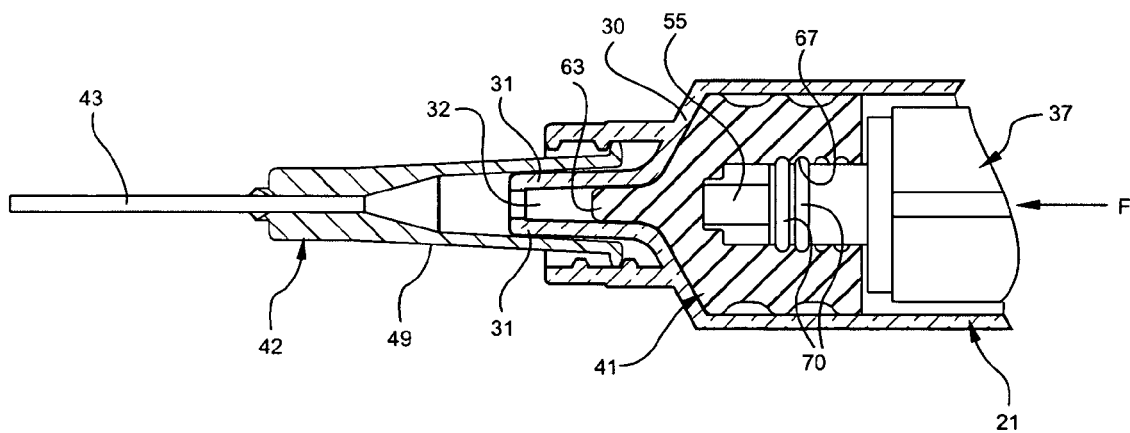
FIG. 5 is an enlarged partial cross-sectional side elevational view of the distal end of the syringe assembly shown after the completion of flush solution delivery and after the application of an additional distally-directed force to the plunger.

In this embodiment the distal end of the stopper is preferably shaped to include a distally directed projection 63 on the distal end of the stopper to fit in passageway 32 when the plunger and the stopper are engaged in the second detent position as best illustrated in FIG. 5. In this embodiment, the inside surface of the stopper preferably includes a proximally direct protuberance 64 configured to contact distal tip 55 of the plunger when the plunger and the stopper are engaged in the second detent position.

The inside surface of the stopper includes a first discontinuity and a second discontinuity located distally from the first discontinuity. The distal end of the plunger includes a discontinuity position so that when the stopper and the plunger are in the first detent position the plunger discontinuity engages the first discontinuity in the stopper and when the stopper and the plunger are in the second detent position, the plunger discontinuity engages the second discontinuity in the stopper. Preferably, the discontinuity at the distal end of the plunger is at least one raised projection. In this embodiment, the at least one raised projection is two raised projections configured in the shape of annular rings 70.

The first discontinuity in the stopper is preferably at least one recess for containing the raised projection on the distal end of the plunger. In this embodiment the at least one recess includes two recesses which are annularly-shaped recesses 65. Likewise, the second discontinuity in the stopper is preferably at least one recess and in this case includes two annularly-shaped recesses 67.

The stopper may be made of any material suitable for providing sealing characteristics while under compression. For example, the stopper may be made of thermoplastic elastomers, natural rubber, synthetic rubber or thermoplastic materials and combinations thereof. The plunger in this embodiment is preferably made of material which is more rigid than the stopper such as polypropylene, polyethylene and the like.

In operation, syringe assembly 20 is connected to a needle assembly and filled with flush solution using known methods. The flush solution may be any solution intended for flushing or maintaining the performance of VAD's. It is preferred that the flush solution be selected from the group consisting of saline flush solution and heparin lock flush solution. These solutions are known in the art and readily available. An example of a saline flush solution is 0.9% Sodium Chloride USP for injection. An example of a heparin lock flush solution is 0.9% Sodium Chloride with 100 USP units of Heparin Sodium per ml or 10 USP units of Heparin Sodium per ml. The syringe with needle assembly attached is used to pierce the pierceable septum or a blunt cannula may be inserted into a pre-split septum of a vial or the neck of a glass ampule containing flush solution, and the flush solution is drawn into the syringe barrel by pulling plunger flange 56 in the proximal direction while holding barrel 21, to draw fluid through the needle cannula into fluid chamber 25.

Alternatively, large numbers of flush syringes may be pre-filled with flush solution during the manufacturing of the syringe using sterile filling methods. Such prefilled syringes may be supplied with a tip cap, such as tip cap 36 releasably connected to tip 31 sealing passageway 32. It is preferred that the tip cap is formed of material selected from a group of thermoplastic materials and elastomeric materials such as natural and synthetic rubber, thermoplastic elastomers, or combinations thereof.

Figure 6:
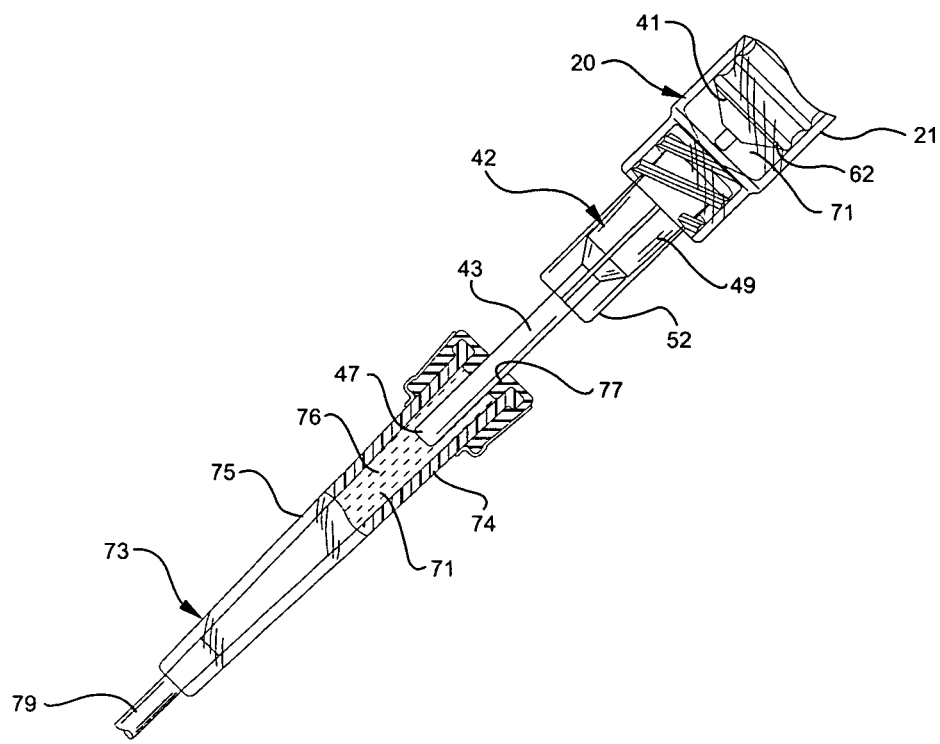
FIG. 6 is a side-elevational view illustrating the syringe assembly in use with a catheter injection site.

The syringe is now ready for use in flushing a catheter of an I.V. set. I.V. sets can be very complicated and may include multiple injection ports, a valve and/or other components. For the purpose of illustrating the present invention a simplified I.V. set 73 is illustrated in FIG. 6. I.V. set 73 comprises an I.V. site 74 which includes a housing 75 having a hollow interior 76 and a septum 77 at its proximal end. An I.V. line 79 having a conduit therethrough extends from the distal end of the housing. For this I.V. set septum 77 is pre-slit for use with blunt cannula. The I.V. site may be a valve having structure for accepting the syringe barrel tip and being activated by the insertion of the tip to establish fluid communication with the catheter, such as the valve taught in U.S. Pat. No. 6,171,287.

Blunt tip 47 of cannula 43 may be inserted through pre-slit septum 77 of I.V. set 73. Alternatively, a sharp tip of a needle cannula may be used to pierce a septum that is not pre-slit, or the tip of the barrel may be engaged with a valve in the IV site. This establishes fluid communication between the interior 76 of the I.V. set and the chamber of the syringe barrel. The syringe barrel 21 is preferably held via finger grips 53. Pressure is then applied to flange 56 of the plunger, for example by a thumb, in the distal direction. This moves plunger 37 having the stopper 41 on its distal end forcing the liquid such as flush solution 71 in chamber 25 out of the chamber, through cannula 43 and into interior 76 of the I.V. set and then through I.V. line 79.

Referring to FIG. 4 the position of the plunger and stopper at the completion of the flush procedure is shown. At the completion of the flush procedure conically shaped distal surface 62 of the stopper contacts conically-shaped inside surface 30 of the distal end wall of the barrel near passageway 31 sealing the passageway, and the stopper remains attached to the plunger at the first detent position. It should be noted that because the total included angle A of the inside surface of the barrel at the distal wall is greater than total included angle B of the conically-shaped distal surface of the stopper in this embodiment, the stopper tends to contact the inside surface near the passageway and seals the passageway. Any incidental flexure of the stopper after the passageway is sealed will not likely create reflux. This is the preferred relationship between the stopper and the barrel. However, this relationship, although preferred, is not necessary to produce the positive displacement of flush solution provided by the present invention. In the embodiment of FIGS. 1-5 the total included angle of the inside surface of the barrel is less than the total included angle of the conically-shaped distal surface of the stopper.

At this point, while clamping the I.V. line, the user applies distally directed force F to flange 56 of the plunger as illustrated in FIG. 5. Additional force F will cause the plunger to move distally with respect to the stopper from the first detent position to the second detent position so that distal tip 55 on the distal end of the plunger contacts the inside surface of the stopper forcing part of the distal end of the stopper into the passageway to move fluid distally in the passageway. In particular, in this embodiment, distal tip 55 contacts proximally-directed protuberance in the stopper cavity deflecting the resilient stopper material so that distally directed projection 63 enters passageway 32 of the barrel tip forcing fluid distally through the I.V. set. The positive displacement of fluid in the passageway in a distal direction will help prevent reflux while the I.V. line is being clamped and the syringe is being removed. After the I.V. line is clamped, the empty syringe assembly may be removed from the I.V. set.

Figure 7:
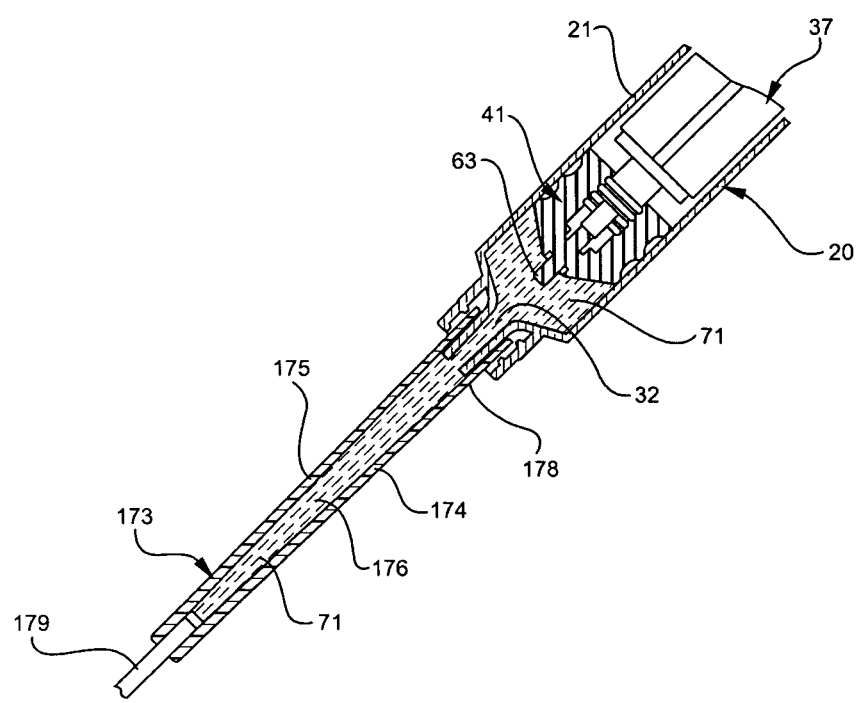
FIG. 7 is a side-elevational view illustrating the syringe assembly in use with another catheter injection site.
Figure 8:
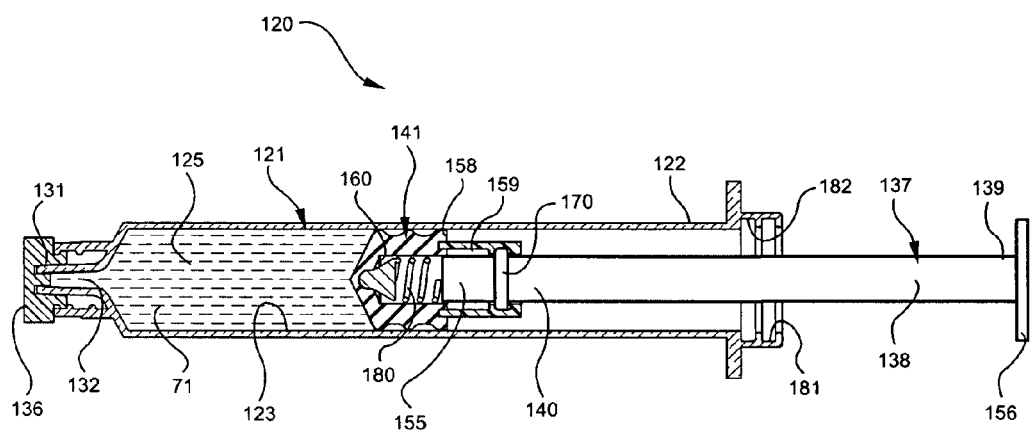
FIG. 8 is a partially cross-sectioned side-elevational view of an alternative syringe assembly of the present invention.
Figure 9:
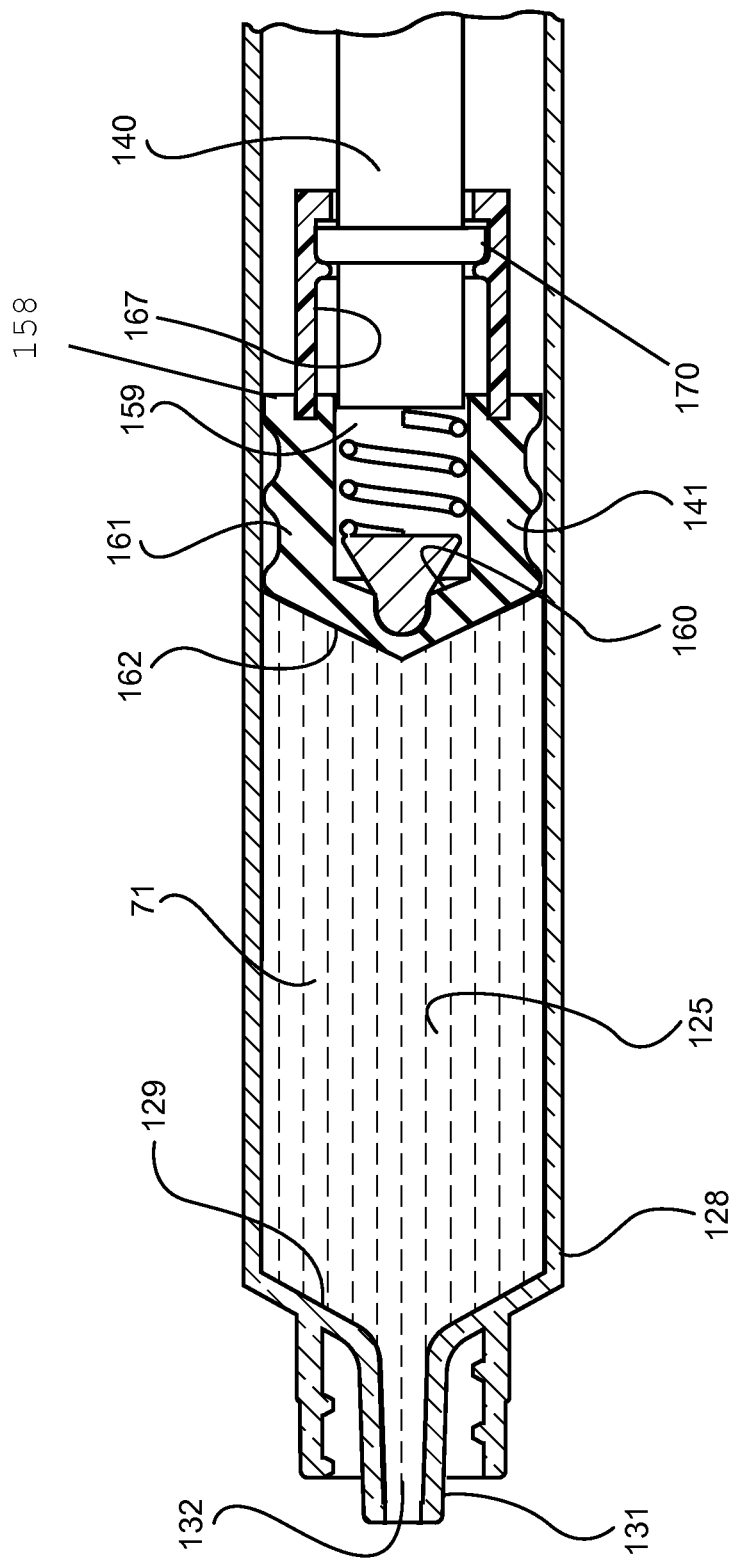
FIG. 9 is an enlarged partial cross-sectional side-elevational view of the syringe assembly of FIG. 8.

FIG. 7 shows an alternative simplified I.V. set to illustrate a flush procedure without a needle assembly. In FIG. 7, I.V. set 173 comprises an I.V. site 174 which includes a housing 175 having a hollow interior 176 and a luer fitting 178 at its proximal end. An I.V. line 179 having a conduit therethrough extends from the distal end of the housing. The example illustrated in FIG. 7 is simplified to demonstrate the invention. In most cases a luer fitting such as luer fitting 178 would be part of a one-way valve in the I.V. set. The elongate tip of the barrel is inserted and engaged with the luer fitting to establish fluid communication between interior 176 of the I.V. set and the chamber of the syringe barrel. Pressure is then applied to flange 56 on the plunger, for example by a thumb, in the distal direction. This moves plunger 37 having stopper 41 on its distal end forcing liquid such as flush solution 71 in chamber 25 out of the chamber, through passageway 32 in the elongate tip into hollow interior 176 of the I.V. set and then through I.V. line 179. The remainder of the flush procedure is substantially identical to the procedures described when using I.V. set 73 of FIG. 6.

FIGS. 8-11 illustrate an alternative embodiment of the syringe assembly of the present invention. In this embodiment syringe assembly 120 comprises a barrel 121 including a cylindrical side wall 122 having an inside surface 123 defining a chamber 125 for retaining fluid. The barrel includes an open proximal end 127 and a distal end 128 including a distal wall 129 with an elongate tip 131 extending distally therefrom and having a passageway 132 therethrough in fluid communication with the chamber. A tip cap 136 is releasably connected to elongate tip 131 for sealing passageway 132.

A plunger 137 includes an elongate body portion 138 having a proximal end 139, a distal end 140 and a resilient stopper 141. A quantity of flush solution 71 is contained within the chamber. The stopper is slidably positioned in fluid-tight engagement with the inside surface of the barrel for drawing fluid into and driving fluid out of the chamber by movement of the stopper relative to the barrel. Part of the elongate body portion of the plunger extends outwardly from the open proximal end of the barrel.

Syringe assembly 120 includes structure for moving fluid distally in the passageway after fluid has been delivered from the chamber and the stopper is in contact with the distal wall. This structure includes the stopper having a distal end 161 with a distal surface 162. The stopper further includes a proximal end 158 having a cavity 159 therein defining an inside surface 160. The distal end of the plunger is connected to the stopper by a complementary detent structure defining a first detent position and a second detent position. A detent structure is configured so that a directed force F applied to the plunger after fluid has been delivered from the chamber causes the plunger to move distally with respect to the stopper from the first detent position to the second detent position so that a distal tip 155 on the distal end of the plunger contacts the inside surface of the stopper forcing part of the distal end of the stopper into the passageway to move fluid distally in the passageway. In this embodiment spring 180 is positioned between distal tip 155 and the distal end of the plunger rod. The spring is configured to compress when the plunger moves to the second detent position with respect to the stopper.

In this embodiment the first detent position is defined by an annular projection 170 on the plunger and an annular recess 165 inside the stopper sized to receive annular projection 170. The second detent position is defined by annular projection 170 and a second annular recess 167 in the stopper. It should be noted that the stopper may be made of more than one piece and more than one material. In this embodiment, a distal end of the stopper is made of resilient material and the proximal end is formed of relatively rigid material such as thermoplastic.

Figure 10:
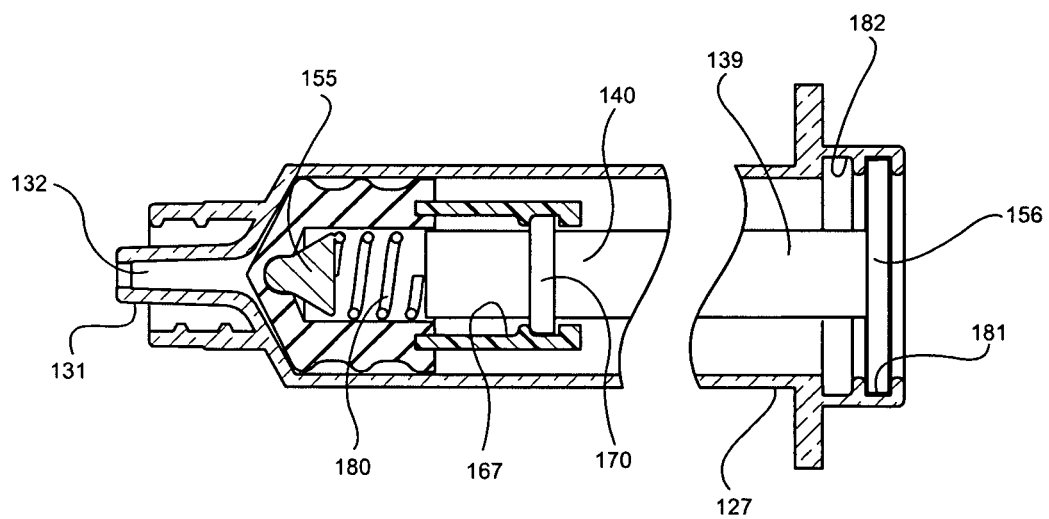
FIG. 10 is an enlarged partial cross-sectional side-elevation view of the syringe assembly of FIG. 8 shown at the completion of flush solution delivery.
Figure 11:
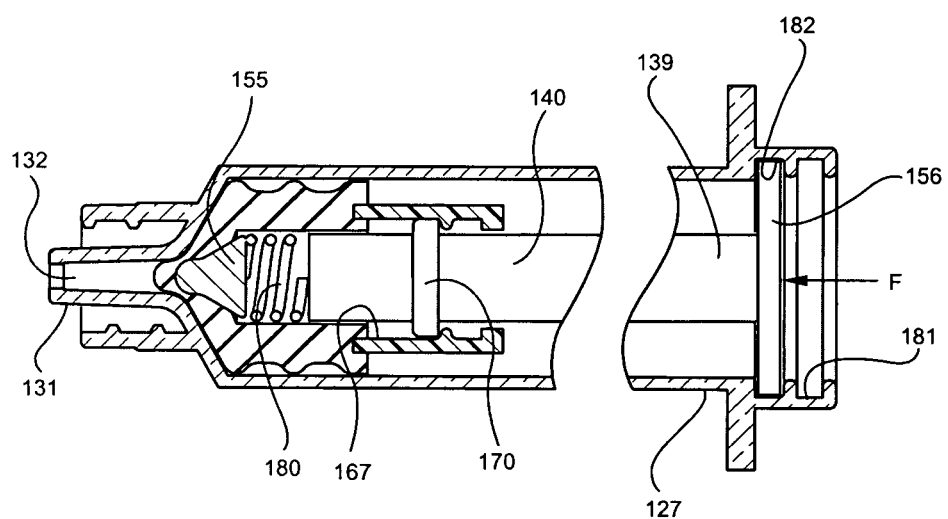
FIG. 11 is an enlarged partial cross-sectional side-elevational view of the syringe assembly of FIG. 8 shown after completion of flush solution delivery and after application of an additional distally directed force to the plunger.

This embodiment contains an additional detent system for controlling the relative position of the plunger with respect to the barrel consisting of a primary detent position and a secondary detent position. The primary detent position is located to engage when fluid has been delivered from the chamber and the stopper is in contact with the distal wall as best illustrated in FIG. 10. The secondary detent position is engaged upon application of an additional distally directed force to the plunger as illustrated in FIG. 11. When the stopper and the plunger are in the second detent position the plunger and the barrel are in the secondary detent position. In this embodiment, the primary detent position is defined by proximal flange 156 on the plunger and annular recess 181 in the proximal end of the barrel. The secondary detent position is defined by flange 156 and a second annular recess 182 in the proximal end of the barrel as illustrated in FIG. 11. The primary and secondary detent positions between the plunger and the barrel can be defined by any combination of complementary structures such as projections, recesses, ratchets, mechanical structures or breaking structures and the flange and recess combination illustrated in this embodiment merely representative of the many possibilities that are within the purview of the present invention. It is also within the scope of the present invention to include an embodiment having only structure for the secondary detent position and not the primary detent position. In this configuration the application of additional force to the plunger after flush solution has been delivered to the catheter, causes the stopper and the plunger to engage in the second detent position and the barrel and the plunger to engage in the secondary detent position. The additional detent system having both a primary and a secondary detent position is preferred when using a stopper having a conically-shaped distal surface and a barrel having a conically-shaped distal wall when the total included angle of the stopper distal surface is equal or greater than the total included angle of the inside surface of the barrel at the distal wall.

In use, this alternate embodiment functions substantially similarly to the preferred embodiment of FIGS. 1-5. The addition of the spring allows more latitude in the design of the product since the material of the stopper does not necessarily have to perform the spring function as in the preferred embodiment.

Figure 12:
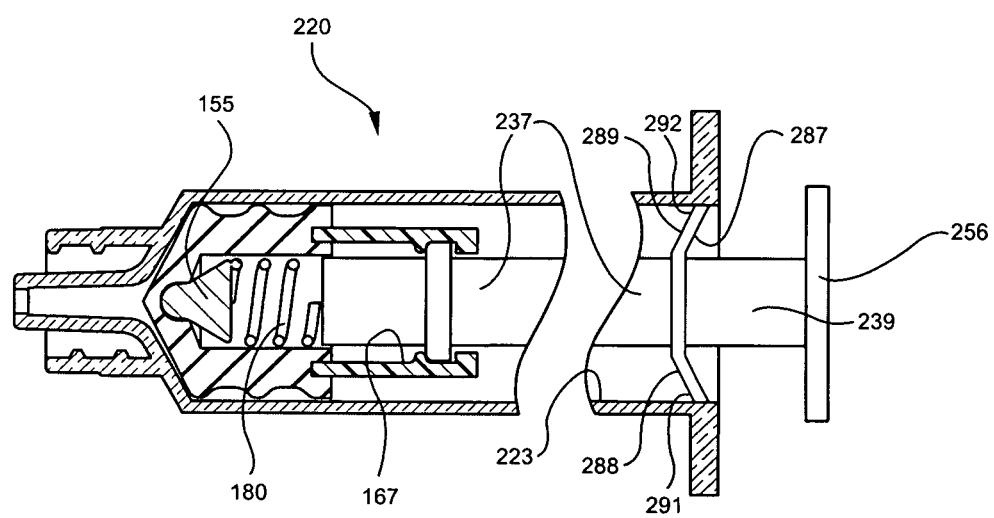
FIG. 12 is an enlarged partial cross-sectional side-elevational view of another alternative embodiment of the syringe assembly of the present invention shown at the completion of flush solution delivery.
Figure 13:
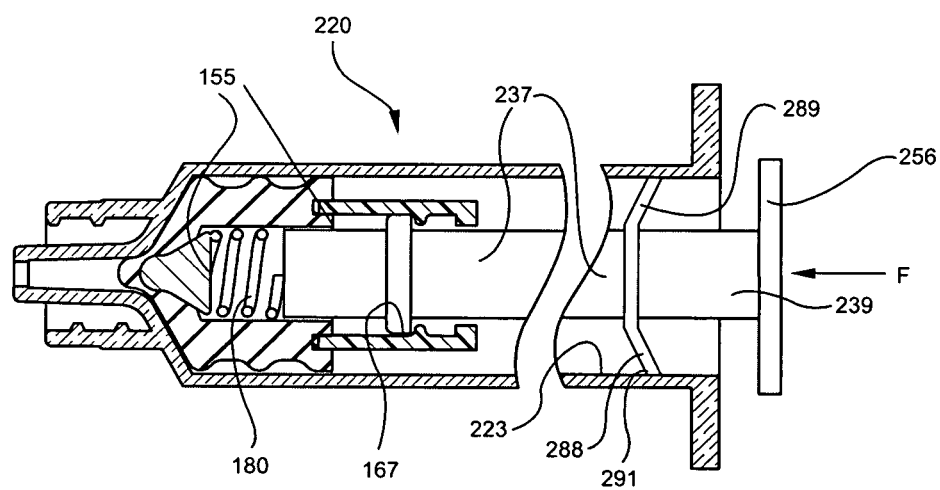
FIG. 13 is an enlarged partial cross-sectional side-elevational view of the syringe assembly of FIG. 12 shown after completion of the flush solution delivery and after application of an additional distally directed force to the plunger.

FIGS. 12 and 13 illustrate another alternative embodiment of the syringe assembly of the present invention. In this embodiment, syringe assembly 220 functions similarly to the embodiment of FIGS. 8-11 except for the structure of the additional detent system for controlling the relative position of the plunger with respect to the barrel. In this alternative embodiment the additional detent system consists of a primary detent position and a secondary detent position. The primary detent position is located to engage when fluid has been delivered from the chamber and the stopper is in contact with the distal wall as illustrated in FIG. 12. The secondary detent position is engaged upon application of an additional distally directed force F to the plunger as illustrated in FIG. 13. When the stopper and the plunger are in the second detent position, the plunger and the barrel are in the secondary detent position. In this embodiment, the primary detent position is established by flexible element 287. The flexible element is connected to or integrally formed with plunger 237 at proximal end 239. Flexible element 287 includes proximally-directed radial projections 288 and 289 having sharp ends 291 and 292 respectively.

In this embodiment, the primary detent position is defined by the sharp ends of radial projections 288 and 289 and inside surface 223 of the barrel at the proximal end of the barrel as illustrated in FIG. 12. The secondary detent position is defined by the sharp ends of the radial projections and a portion of inner surface 223 of barrel 221 which is positioned distally from the primary detent position as illustrated in FIG. 13. In this embodiment the secondary detent position can occur at any position which is distal to annular projection 293. This structure is less tolerance-dependent because the detent positions can occur over a range of positions within the barrel. The flexible element 287 may be made of sheet metal such as stainless steel. The harder metal will enhance the grip of the sharp ends of the projections to resist proximal motion of the plunger with respect to the barrel. The flexible element may be circularly shaped like a flexible flange so that the sharp edge can go up to 360 degrees around the plunger. Further, one or more projections may radiate from the proximal end of the stopper so long as the net result is the restraint of the motion of the plunger with respect to the barrel. Discontinuities such as recesses and/or projections may also be placed in the barrel to enhance the function of the radial projections.

What is claimed is:
1. An I.V. flush syringe assembly comprising:
a barrel including a cylindrical side wall having an inside surface defining a chamber for retaining fluid, an open proximal end and a distal end including a distal wall with an elongate tip extending distally therefrom, the elongate tip defining a passageway therethrough in fluid communication with the chamber; and
a plunger including an elongate body portion extending outwardly from the open proximal end of the barrel, a proximal end, a distal end having a discontinuity and a spring disposed at the distal end;
a resilient stopper slidably positioned in fluid-tight engagement with the inside surface of the barrel for drawing fluid into and driving fluid out of the chamber by movement of the stopper relative to the barrel;
wherein the stopper includes a distal end having a distal surface including a distally directed projection shaped to fit in the chamber of the barrel, a first discontinuity and a second discontinuity located distally from the first discontinuity and a proximal end defining a cavity therein;
wherein the distal end of the plunger is connected to the stopper by a complementary detent structure defining a first detent position wherein the plunger discontinuity engages the first discontinuity and a second detent position wherein the plunger discontinuity engages the second discontinuity;
wherein the detent structure is configured so that a distally directed force applied to the plunger after fluid has been delivered from the chamber causes the spring to compress and the plunger to move distally with respect to the stopper from the first detent position to the second detent position so a distal tip on the distal end of the plunger contacts the inside surface of the stopper forcing the distally directed projection on the distal end of the stopper into the passageway of the elongate tip to move fluid distally in the passageway after fluid has been delivered from the chamber and the stopper is in contact with the distal wall.

2. The syringe assembly of claim 1 wherein the inside surface of the stopper includes a proximally directed protuberance configured to contact the distal tip of the plunger when the plunger and the stopper are engaged in the second detent position.

3. The syringe assembly of claim 1 wherein the stopper includes a conically shaped distal surface and the inside surface of the barrel at the distal wall being conically shaped wherein the total included angle of the inside surface of the barrel at the distal wall is greater than the total included angle of the stopper distal surface.

4. The syringe assembly of claim 1 wherein the discontinuity on the distal end of the plunger includes a raised projection.

5. The syringe assembly of claim 4 wherein the raised projection is an annular ring.

6. The syringe assembly of claim 5 wherein the first discontinuity is a recess for containing the raised projection on the distal end of the plunger.

7. The syringe assembly of claim 6 wherein the recess is annularly shaped.

8. The syringe assembly of claim 1 including flush solution in the chamber.

9. The syringe assembly of claim 8 further including a tip cap releasably connected to the tip of the syringe barrel for sealing the passageway.

10. The syringe assembly of claim 9 wherein the flush solution is selected from the group consisting of saline flush solution and heparin lock flush solution.

11. The syringe assembly of claim 1 wherein the stopper is made of material selected from the list consisting of thermoplastic elastomers, natural rubber, synthetic rubber, thermoplastic materials and combinations thereof.

12. The syringe assembly of claim 1 further comprising a needle assembly including a cannula having a proximal end, a distal end and a lumen therethrough, and a hub having an open proximal end containing a cavity and a distal end attached to the proximal end of the cannula so that the lumen is in fluid communication with the cavity, the needle assembly being removably attached to the tip of the barrel through engagement of the tip to the cavity so that the lumen is in fluid communication with the chamber.

13. An I.V. flush syringe assembly comprising:
- a barrel including a cylindrical side wall with an inside surface defining a chamber for retaining fluid, an open proximal end and a distal end including a distal wall with an elongate tip extending distally therefrom, the elongate tip defining a passageway therethrough in fluid communication with the chamber;
- wherein the distal wall of the barrel defines a total included angle A;
- a plunger including an elongate body portion extending outwardly from the open proximal end of the barrel, a proximal end, a distal end having a discontinuity, a distal tip and a spring positioned between the distal tip and the distal end;
- a resilient stopper operably engaged to the plunger and slidably positioned in fluid-tight engagement with the inside surface of the barrel for drawing fluid into and driving fluid out of the chamber by movement of the stopper relative to the barrel;
- wherein the stopper includes a distal end having a distal surface including a distally directed projection shaped to fit in the chamber of the barrel, a first discontinuity and a second discontinuity located distally from the first discontinuity and a proximal end defining a cavity therein;
- wherein the distal end of the stopper defines a total included angle B;
- wherein the distal end of the plunger is connected to the stopper by a complementary detent structure defining a first detent position in which the plunger discontinuity engages the first discontinuity and a second detent position in which the plunger discontinuity engages the second discontinuity;
- wherein the detent structure is configured so that a distally directed force applied to the plunger after fluid has been delivered from the chamber causes the spring to compress and the plunger to move distally with respect to the stopper from the first detent position to the second detent position so a distal tip on the distal end of the plunger contacts the inside surface of the stopper forcing the distally directed projection on the distal end of the stopper into the passageway of the elongate tip to move fluid distally in the passageway after fluid has been delivered from the chamber and the stopper is in contact with the distal wall; and
- wherein the total included angle A is greater than the total included angle B.

14. The syringe assembly of claim 13 wherein the inside surface of the stopper includes a proximally directed protuberance configured to contact the distal tip of the plunger when the plunger and the stopper are engaged in the second detent position.

15. The syringe assembly of claim 14 wherein the discontinuity on the distal end of the plunger includes a raised projection formed by an annular ring.

16. The syringe assembly of claim 15 wherein the first discontinuity is a recess for containing the raised projection on the distal end of the plunger.

17. The syringe assembly of claim 16 wherein the recess is annularly shaped.

18. The syringe assembly of claim 17 including flush solution in the chamber.

19. The syringe assembly of claim 18 wherein the flush solution is selected from the group consisting of saline flush solution and heparin lock flush solution.

20. The syringe assembly of claim 19 further comprising a needle assembly including a cannula having a proximal end, a distal end and a lumen therethrough, and a hub having an open proximal end containing a cavity and a distal end attached to the proximal end of the cannula so that the lumen is in fluid communication with the cavity, the needle assembly being removably attached to the tip of the barrel through engagement of the tip to the cavity so that the lumen is in fluid communication with the chamber.

* * * * *